(12) United States Patent
Bottom

(10) Patent No.: US 8,365,724 B2
(45) Date of Patent: Feb. 5, 2013

(54) MEDICAL VAPORIZER AND METHOD OF CONTROL OF A MEDICAL VAPORIZER

(75) Inventor: Douglas K. Bottom, Watertown, WI (US)

(73) Assignee: General Electric Company, Schenectady, NY (US)

( * ) Notice: Subject to any disclaimer, the term of this patent is extended or adjusted under 35 U.S.C. 154(b) by 436 days.

(21) Appl. No.: 12/648,602

(22) Filed: Dec. 29, 2009

(65) Prior Publication Data
US 2011/0155131 A1   Jun. 30, 2011

(51) Int. Cl.
*A61M 15/00* (2006.01)
(52) U.S. Cl. .............. 128/203.14; 128/203.25
(58) Field of Classification Search ........... 128/203.12–203.16, 203.25
See application file for complete search history.

(56) References Cited

U.S. PATENT DOCUMENTS

| | | | |
|---|---|---|---|
| 5,060,506 A | 10/1991 | Douglas | |
| 5,060,514 A | 10/1991 | Aylsworth | |
| 5,247,826 A * | 9/1993 | Frola et al. | 73/24.01 |
| 5,369,979 A | 12/1994 | Aylsworth et al. | |
| 5,546,931 A * | 8/1996 | Rusz | 128/203.12 |
| 5,581,014 A | 12/1996 | Douglas | |
| 5,644,070 A | 7/1997 | Gibboney et al. | |
| 5,967,141 A * | 10/1999 | Heinonen | 128/203.12 |
| 6,279,378 B1 | 8/2001 | Sheen et al. | |
| 7,063,668 B2 | 6/2006 | Cardelius et al. | |
| 7,434,580 B2 | 10/2008 | Downie et al. | |

* cited by examiner

*Primary Examiner* — Theodore Stigell
(74) *Attorney, Agent, or Firm* — Andrus, Sceales, Starke & Sawall, LLP

(57) ABSTRACT

An anesthetic vaporizer and a method of control thereof includes measuring a composition of the carrier gas with a first sensor and measuring a composition of a combined gas with a second sensor, and using these values with a controller to operate a flow valve for the regulation of the flow of an anesthetic agent into the combined gas.

20 Claims, 3 Drawing Sheets

US 8,365,724 B2

MEDICAL VAPORIZER AND METHOD OF CONTROL OF A MEDICAL VAPORIZER

BACKGROUND

The present disclosure is related to the field of medical anesthesia. More specifically, this disclosure is related to an anesthetic vaporizer and control thereof.

An anesthetic agent, or agents, may be delivered to a patient in order to produce the effects of sedation, analgesia, and neuro-muscular block, broadly referred to as anesthesia. Different anesthetic agents produce different effects and degrees of effects, and therefore, must be carefully delivered to the patient. When the anesthetic agent, or agents, are delivered in a gaseous form for patient inhalation, the anesthetic agent is combined with one or a combination of carrier gases for delivery to the patient. A medical vaporizer combines these two or more gases before delivery to the patient.

BRIEF DISCLOSURE

The present disclosure includes an anesthetic vaporizer. The anesthetic vaporizer includes a carrier gas conduit, an anesthetic source, and a flow valve disposed between the anesthetic source and the carrier gas conduit. A first sensor is in communication with the carrier gas conduit and a second sensor is in communication with the carrier gas conduit. A controller receives a first sensor signal and a second sensor signal and the controller is connected to the flow valve and operates the flow valve in response to the received first and second sensor signals.

A system for the delivery of an anesthetic agent includes a breathing circuit configured to deliver a combined gas to a patient. A carrier gas conduit is connected to a carrier gas source and is further connected to the breathing circuit. The carrier gas conduit conveys a flow of carrier gas to the breathing circuit. An anesthetic gas inlet is in fluid communication between an anesthetic source and the breathing circuit. A flow valve is in communication between the anesthetic source and the anesthetic gas inlet. The flow valve is operable to control the flow of the anesthetic gas through the anesthetic gas inlet. A first sensor produces a first sensor signal indicative of the composition of carrier gas. A second sensor produces a second sensor signal indicative of a composition of combined gas. A controller receives the first sensor signal and the second sensor signal and operates the flow valve to control the composition of the combined gas.

A method of controlling the delivery of an anesthetic agent includes establishing a target anesthetic agent concentration. Next, a first ultrasound sensor measures an acoustical time of flight of an ultrasound signal through a carrier gas and a second ultrasound sensor measures an acoustical time of flight of an ultrasound signal through a combined gas. A processor calculates a target acoustical time of flight for the ultrasound signal through the combined gas and compares the target acoustical time of flight and the measured acoustical time of flight of the ultrasound signal through the combined gas. A flow valve adjusts the flow of the anesthetic agent into the combined gas.

DETAILED DISCLOSURE

Figure 1:
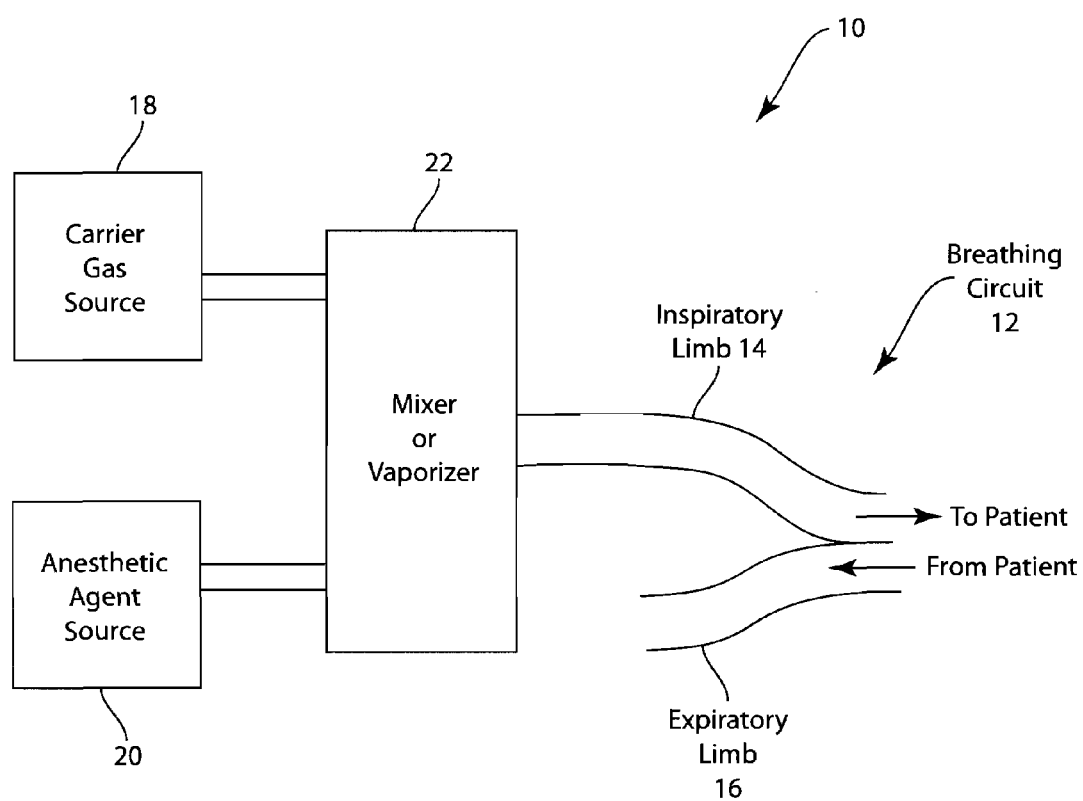
FIG. 1 depicts an anesthesia delivery system.

FIG. 1 depicts an anesthesia delivery system 10. The anesthesia delivery system 10 includes a breathing circuit 12 with an inspiratory limb 14 and an expiratory limb 16. The inspiratory limb 14 delivers a combined gas, as will be described in further detail herein, to a patient. While in some systems, the patient is permitted to exhale into the ambient room atmosphere, requiring no expiration limb 16, often the patient exhalation is directed through the expiratory limb 16. The expiratory limb 16 of the breathing circuit 12 directs the expired breath from the patient to treatment devices (not depicted) such as, but not limited to, anesthetic gas scavenging devices or carbon dioxide absorbers that treat the expired breath before releasing the gas into the room or recirculating the excess anesthetic agent and/or other exhaled gases back to the patient through the breathing circuit 12.

The anesthesia delivery system 10 further includes a carrier gas source 18 and an anesthetic agent source 20. The carrier gas source 18 may include a source or sources of one or more of a variety of gases to be delivered to the patient. These gases may include, but are not limited to, oxygen, nitrous oxide, air, carbon dioxide, and heliox. Each of these carrier gases, alone or in combination with other gases, provide ventilatory benefits to the patient, as well as provide a base gas for the delivery of the anesthetic agent. The combination of the carrier gas with the anesthetic agent not only provides the patient with the respiratory benefits derived from the carrier gas mixture and anesthesia treatment, but also provides a setting wherein the concentration of the anesthetic agent may be controlled as a percentage of the resulting combined gas, when the anesthetic agent is mixed with the carrier gas and provided to the patient.

The anesthetic agent source 20 may contain any of a variety of anesthetic agents, such as, but not limited to, Desflurane, Enflurane, Halothane, Isoflurane, Sevoflurane, and Xenon. These gases are often provided one at a time, as particular combinations of anesthetic agents may degrade the individual agents and produce undesirable by-products.

However, the anesthetic agent source 20 may include a plurality of anesthetic agents, which are delivered in a succession such as to provide more sophisticated control of the anesthesia of the patient using the properties of a plurality of anesthetic agents.

The anesthetic agents of Desflurane, Enflurane, Halothane, Isoflurane, and Sevoflurane sources form a saturated vapor as a carrier gas is pass over a liquid sump filled with the anesthetic agent. Xenon is provided from a pressurized gas cylinder. Desflurane above its boiling point is also provided in gaseous form.

The carrier gas provided from the carrier gas source 18 and the anesthetic agent provided from the anesthetic agent source 20 are combined in a mixer or vaporizer 22. In the mixer or vaporizer 22, the pressure and concentration of the resulting combined gas is controlled such that a target concentration of the constituent carrier gas and anesthetic agent is achieved for delivery to the patient through the inspiratory limb 14.

Due to the medical condition, or the resulting sedation of the patient, an anesthesia delivery system 10 may be combined with a ventilation system, such that respiratory care or assistance may be provided to the patient in conjunction with the delivery of anesthesia. While not depicted in FIG. 1, such a ventilatory system may include additional structures such as a pressure generating bellows and pressure or flow sensors and the resulting control circuitry required to provide the ventilatory support or care to the patient.

Figure 2:
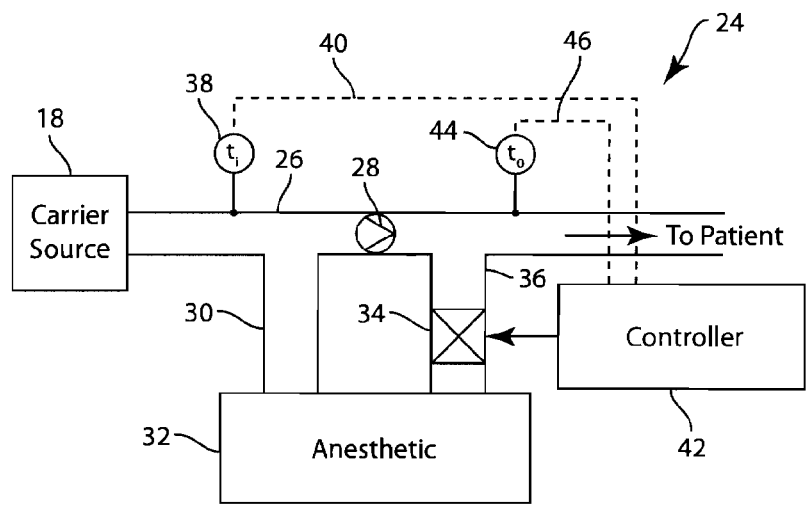
FIG. 2 depicts a first embodiment of an anesthetic vaporizer in a split flow configuration.

FIG. 2 depicts an embodiment of an anesthetic vaporizer 24 in a split flow or plenum configuration. The carrier gas source 18 provides a flow of carrier gas, as described above, through a carrier gas conduit 26. Disposed within the carrier gas conduit 26 is a pressure regulation device 28 such as a flow valve, a one-way check valve, or a bottleneck in the carrier gas conduit 26. The pressure regulation device 28 diverts a portion of the carrier gas from the carrier gas conduit 26 through a diversion conduit 30 into an anesthetic sump 32. The anesthetic sump 32 holds a liquid source of anesthetic agent. As the diverted carrier gas passes through the anesthetic sump, the liquid anesthetic agent saturates the diverted carrier gas with anesthetic agent vapor. Anesthetic agents such as Desflurane, Enflurane, Halothane, Isoflurane, and Sevoflurane have typically low vapor pressures and therefore readily saturate the carrier gas with anesthetic agent as the diverted carrier gas passes through the anesthetic sump 32. The anesthetic sump 32 may be heated to a temperature based upon the specific anesthetic agent such as to create a stable production of anesthetic agent vapor within the sump 32.

The outlet of the diverted carrier gas, now saturated with anesthetic agent from the anesthetic sump 32, is controlled by a flow valve 34 that is located between the anesthetic sump 32 and an anesthetic gas inlet 36 that reconnects the diverted carrier gas, now saturated with anesthetic agent, back to the carrier gas conduit 26 downstream of the pressure regulation device 28. At this intersection, the carrier gas that passed through the pressure regulation device 28 is combined with the diverted carrier gas that is now saturated with anesthetic agent. The combination of these two gas flows form combined gas that is delivered to the patient via the breathing circuit 12 (FIG. 1).

Two sensors are disposed along the carrier gas conduit 26. In an embodiment, these two sensors are ultrasonic time of flight sensors that measure the time required for an ultrasonic wave to pass across the carrier gas conduit 26 through the gas flowing in the conduit and return to the sensor. This time of flight is dependent upon the composition or make up of the gas flowing through the carrier gas conduit 26 at the measured point.

In an embodiment, a first sensor 38 is located at the carrier gas conduit 26 at a location near the carrier gas source 18, upstream of the pressure regulation device 28 and the diversion conduit 30. The first sensor 38 produces a sensor signal 40 that is directed to a controller 42. The sensor signal 40 is indicative of the composition of the carrier gas produced from the carrier source 18. This gives the controller 42 a base line determination of the starting or initial gas concentration of the carrier gas. Alternatively, the sensor signal 40 is indicative of the time-of-flight across the carrier gas conduit 26 through the carrier gas.

A second sensor 44 is also disposed within the carrier gas conduit 26; however, the second sensor 44 is located downstream of the pressure regulation device 28 and the anesthetic gas inlet 36. Thus, the second sensor 44 produces a time of flight measurement across the carrier gas conduit 26 filled with the combined gas which, with the addition of the anesthetic agent, comprises a different gas composition than the carrier gas measured by the first sensor 38. This time of flight measurement is sent to the controller 4442 via sensor signal 46. The time-of-flight measurement embodied on the sensor signal 46 from the second sensor 44 is indicative of the composition of the combined gas, which will be ultimately delivered to the patient via the breathing circuit (FIG. 1).

A comparison of the time-of-flight measurements from the first sensor 38 and the second sensor 44 reveals the difference in the measured acoustical time-of-flight of the combined gas composition that is attributable to the anesthetic agent saturating the diverted portion of the carrier gas. From this comparison, the controller 42 is able to determine the composition of the combined gas in terms of a percentage composition of the anesthetic agent. By controlling the flow valve 34, the controller 42 can effect a manipulation of the combined gas composition, such that a target anesthetic agent concentration may be achieved.

A command (X) produced by the controller 42 is derived from the received first sensor signal ($t_i$) 40 and second sensor signal ($t_o$) 46 in conjunction with a received input of the desired anesthetic concentration of the combined gas ($C_o$) may be described as found in equation (1). The notation "f( . . . )" denotes is a function of and the exact form of "f( . . . )" will vary depending on context.

$$X = f(t_i, t_o, C_o) \tag{1}$$

The command (X) to the flow valve is created using a negative feedback control scheme. A number of forms exist for the error signal (e) and some may be designated as follows:

$$e = t_o - \hat{t}_o \tag{2}$$

$$e = (t_o - t_i) - (\hat{t}_o - t_i)$$

$$e = (t_o/t_i) - (\hat{t}_o/t_i)$$

The "hat" designates calculated target values when the vaporizer anesthetic concentration of the combined gas matches the inputted target anesthetic concentration.

Determining the second quantity, the calculated targeted value, requires an examination of relevant gas physics and gas properties. Acoustic wave speed in a gas is represented in the equation below, with the following definitions: v is speed, γ is heat capacity ratio, R is the universal gas constant, T is absolute temperature, and M is molecular weight.

$$v = \sqrt{\frac{\gamma \cdot R \cdot T}{M}} \tag{3}$$

For pure gases, γ and M are tabulated. For gas mixtures, additional relationships from physics must be applied. These are shown below, with the following definitions: $\gamma_M$ is mixed gas heat capacity ratio, $\gamma_i$ are component gas heat capacity ratios, $X_i$ are component gas volumetric fractions (i.e. concentrations), $M_M$ is mixed gas molecular weight, $M_i$ are component gas molecular weights. Note that equations (4) and (5) can be applied to mixing pure carrier gases as well as mixing anesthetic gas into carrier gas. In the latter case, the $X_i$ are easily related to $C_o$.

$$\gamma_M = 1 + \left(\frac{X_1}{(\gamma_1 - 1)} + \frac{X_2}{(\gamma_2 - 1)}\right)^{-1} \tag{4}$$

$$M_M = X_1 \cdot M_1 + X_2 \cdot M_2 \tag{5}$$

Pursuing the preferred first form in equation (2), from the above equations, it can be seen that the values for $t_i$ and $t_o$ may be reduced to the following functions where $\gamma_A$ is anesthetic gas heat capacity ratio and $M_A$ is anesthetic gas molecular weight.

$$t_i = f(\gamma_i, M_i, T) \quad (6)$$

$$\hat{t}_o = f(\gamma_i, \gamma_A, M_i, M_A, T, C_o) \quad (7)$$

This latter equation for the calculated target $t_o$ still requires an input of the carrier gas properties ($\gamma$, M) and an absolute temperature measurement (T). However, by substituting the acoustic wave time-of-flight for the input carrier gas ($t_i$), substituting a nominal value for the absolute temperature, and applying basic curve fitting techniques, an output anesthetic concentration meeting accuracy specifications is sufficiently achieved. Thus, the final form, presented below, may be calculated specific to each anesthetic agent.

$$\hat{t}_o = f_A(t_i, C_o) \quad (8)$$

By the combining of equations (2) and (8), the negative feedback control signal provided by the controller 42 for control of the flow valve 34 can be represented as equation (9) which requires only the first sensor signal 40 and second sensor signal 46 values of time-of-flight and the input target anesthetic concentration value.

$$e = t_o - f_A(t_i, C_o) \quad (9)$$

The negative feedback control operates such that the controller 42 produces a flow valve 34 control signal such as to reduce the error (e) to zero. At that point, the target anesthetic concentration value has been achieved by the vaporizer.

Thus, the presently disclosed vaporizer and method of control achieves anesthetic concentration control in a simplified and efficient manner. This control lends itself to a variety of embodiments as disclosed with respect to FIG. 2, as well as additional embodiments both highlighted below as well as would be recognized by one of ordinary skill in the art.

Figure 3:
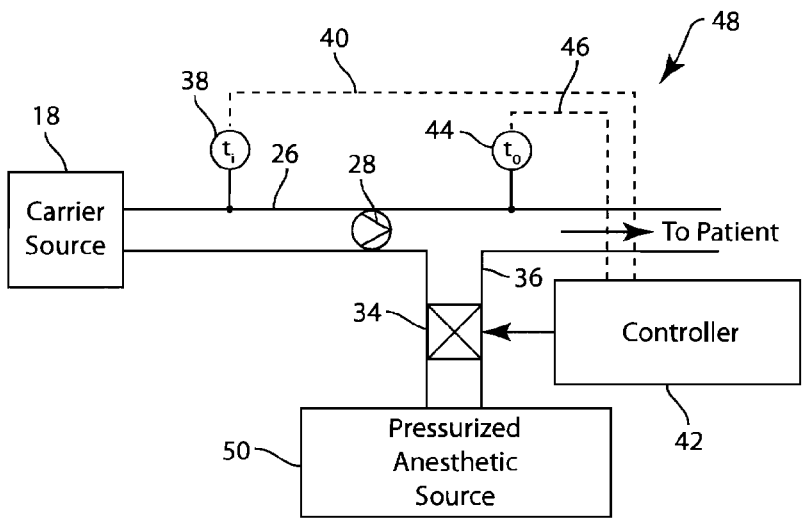
FIG. 3 depicts a second embodiment of an anesthetic vaporizer in a dual circuit configuration.

FIG. 3 depicts a second embodiment of an anesthetic vaporizer 48. The embodiment of the anesthetic vaporizer 48 depicts a dual circuit, gas blender type vaporizer, such as may be used with a pressurized anesthetic source 50. Such a pressurized anesthetic source may include such anesthetic sources as a pressurized tank of Xenon or a source of Desflurane above its boiling point.

In the anesthetic vaporizer 48 of FIG. 3, wherein like numerals reference like structures as described above, the pressurized anesthetic source 50 embodies its own mechanism for propelling the anesthetic agent into combination with the carrier gas. No diversion of the carrier gas into the anesthetic source 50 is required. Therefore, the controller 42 merely regulates the flow of the pressurized anesthetic agent out of the pressurized anesthetic source 50 and through the anesthetic gas inlet 36 into the carrier gas conduit 26 by controlling the flow valve 34 as described above.

Figure 4:
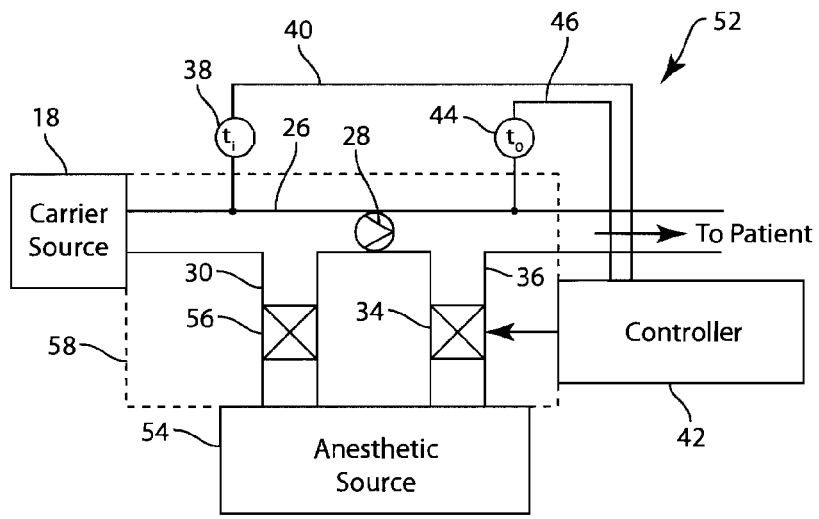
FIG. 4 depicts a third embodiment of an anesthetic vaporizer in a combined configuration, and,
FIG. 5 is a flow chart depicting a method of controlling the delivery of an anesthetic agent.

FIG. 4 depicts a still further embodiment of an anesthetic vaporizer 52 that combines both the split flow, plenum anesthetic vaporizer 24 of FIG. 2 and the dual circuit, gas blender anesthetic vaporizer 48 of FIG. 3 into a single combinational anesthetic vaporizer 52. In the combinational anesthetic vaporizer 52, at FIG. 4, wherein like reference numerals reference like structures as described above, the anesthetic source 54 is an interchangeable anesthetic source 54, such that an anesthetic sump (as depicted in FIG. 2), or alternatively, a pressurized anesthetic source (as depicted in FIG. 3) may be connected to the anesthetic vaporizer 52. Based upon the type of anesthetic source 54 attached to the anesthetic vaporizer 52, a shut-off valve 56 located within the diversion conduit 30 between the carrier gas conduit 26 and the anesthetic source 54 may be controlled between an open and a closed position.

The shut-off valve 56 may be operated in an open position when the anesthetic source 54 is an anesthetic sump, such that the diversion conduit 30 is open from the carrier gas conduit 26 to the anesthetic sump, providing the required diverted flow of carrier gas for anesthetic saturation. In an embodiment wherein the anesthetic source 54 is a pressurized anesthetic source, the shut-off valve 56 is operated in a closed position, thereby closing off carrier gas flow through the diversion conduit 30 and directing the carrier gas flow through the pressure regulation device 28 where the carrier gas is mixed with the pressurized anesthetic agent from the anesthetic source 54 through the anesthetic gas inlet 36.

Thus, the anesthetic vaporizer 52 offers a combinational vaporizer that is able to control the delivery of a combined gas comprising carrier gas and anesthetic agent to a patient that achieves a target anesthetic gas concentration regardless of the attached anesthetic source, and using the same sensor set and control independent from the specific anesthetic source and anesthetic agent used in the vaporizer 52.

Embodiments of the anesthetic vaporizer 52 may further include control by the controller 42 of the operation of the pressure regulation device 28 and the shut-off valve 56 in a similar manner as in the disclosed control of the flow valve 34. In such embodiments, the target anesthetic agent concentration may be achieved through a combination of controls of the pressure regulation device 28, shut-off valve 56, and flow valve 34 in order to achieve the target anesthetic agent concentration in an efficient manner. Additionally, such a control system allows for the additional control of not only the concentration of anesthetic agent delivered to the patient, but the time basis amount of the anesthetic agent, as well as the total volume of the combined gas provided to the breathing circuit.

As further depicted in FIG. 4, the anesthetic vaporizer 52 further includes a manifold 58 that comprises the carrier gas conduit 26, diversion conduit 30, and anesthetic gas inlet 36. The manifold 58 further has additional components integral with or inserted into the manifold, such as shut-off valve 56, flow valve 34, pressure regulation device 28, first sensor 38, and second sensor 44. In such an embodiment that includes manifold 58, or another similar manifold comprising fewer or more components as disclosed herein, may further regulate the temperature of the carrier gas and the anesthetic agent by directing them through the same manifold. With this additional temperature regulation, the sensor signals 40 and 46 from the first sensor 38 and the second sensor 44 have minimized error due to differences in gas temperature from the carrier gas measured at the first sensor 38 and the combined gas measured at the second sensor 44.

Figure 5:
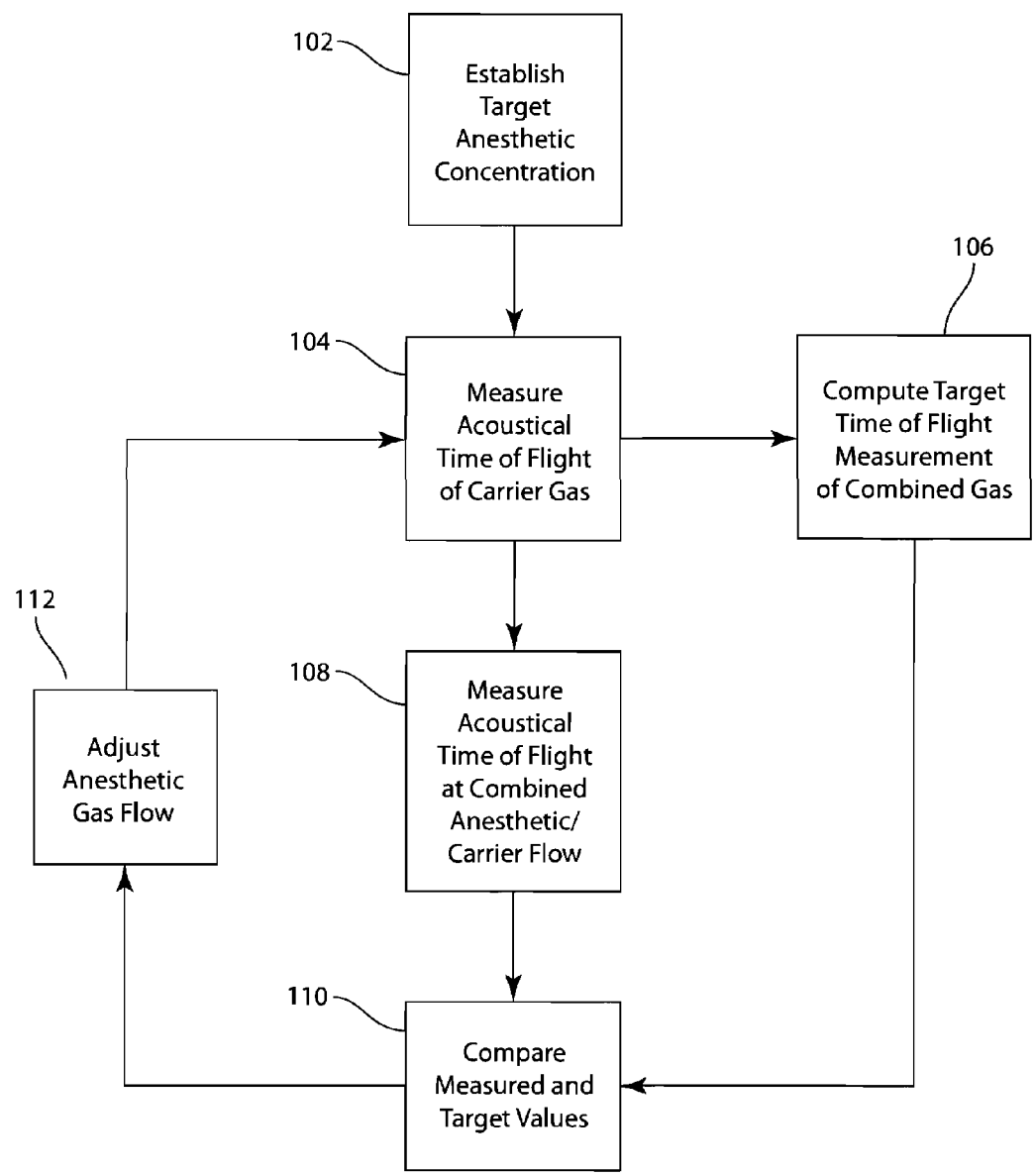

FIG. 5 depicts a method 100 of controlling the delivery of an anesthetic agent. The method begins with step 102 wherein a target anesthetic concentration is established.

The establishment of a target anesthetic concentration may include receiving an input into a controller both the type of anesthetic agent located in the anesthetic source as well as the desired concentration thereof to be delivered to the patient. Each anesthetic agent has a different level of potency resulting in different effective concentrations to be delivered to the same patient for different anesthetic agents. Furthermore, absorption rates of different anesthetic agents, resulting in varied Mean Alveolar Concentrations (MAC) for each of the anesthetic agents causes a further need for adjustment to an established target anesthetic concentration of a specified anesthetic agent.

At step 104, the acoustical time-of-flight of the carrier gas is measured. The acoustical time-of-flight of the carrier gas may be measured using an ultrasonic transducer that is located at a suitable location for measuring the time-of-flight through the flow of gas provided by the carrier gas source. One suitable location would be along the carrier gas conduit, through which the full volume of carrier gas ultimately delivered to the patent passes. This may be just downstream from the carrier gas source, or alternatively, upstream of the diversion conduit.

After the acoustical time-of-flight through the carrier gas is measured at step 104, the measured time-of-flight through the carrier gas is used in step 106 by the controller to compute a target time-of-flight measurement for the combined anesthetic and carrier gases. The computed target time-of-flight measurement in step 106 can be computed as detailed above using the identified anesthetic agent, the established target anesthetic concentration from step 102 and the measured acoustical time-of-flight of the carrier gas from step 104. The controller, in performing step 106, uses the measured acoustical time-of-flight of the carrier gas from step 104 to provide an indication of the composition of the carrier gas, such that the target time-of-flight for the combined gas corresponds to the inputted target anesthetic agent concentration.

At step 108, the acoustical time-of-flight of the combined anesthetic and carrier gases is measured with an ultrasound sensor. This measurement is provided to the controller which also receives the computed target time-of-flight measured from step 106 and compares the measured and target values for the acoustical time-of-flight of the combined anesthetic and carrier gases. This comparison between the measured and target values creates an indication of error which is used through a negative feedback loop in step 112 to adjust the anesthetic gas flow, such as by controlling a pneumatic flow valve between the anesthetic source and the carrier gas conduit.

After this adjustment of the anesthetic gas flow, the method is repeated to perform a new measure of the acoustical time-of-flight of the combined anesthetic and carrier gas, which is again compared to the computed target time-of-flight measurement. Additionally, the steps of measuring the acoustical time-of-flight of the carrier gas, 104, and computing the target time-of-flight measurement 106 may be repeated at every cycle, or at a varying schedule of cycles such as to balance the need of updating these values versus repeating computations that remain relatively static as compared to other more variable values in the system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. An anesthetic vaporizer, comprising:
   a carrier gas conduit configured to deliver a flow of carrier gas;
   an anesthetic source, comprising an anesthetic agent;
   a flow valve disposed between the anesthetic source and an anesthetic gas inlet in the carrier gas conduit, the flow valve operable to control a flow of the anesthetic agent into the carrier gas;
   a first sensor in communication with the carrier gas conduit upstream of the anesthetic gas inlet and the first sensor produces a first sensor signal indicative of a composition of the carrier gas upstream of the anesthetic gas inlet;
   a second sensor in communication with the carrier gas conduit downstream of the anesthetic gas inlet and the second sensor produces a second sensor signal indicative of a composition of the combined carrier gas and anesthetic agent; and
   a controller that receives the first sensor signal and the second sensor signal, the controller further connected to the flow valve and operates the flow valve in response to the received first sensor signal and second sensor signal.

2. The anesthetic vaporizer of claim 1, wherein the controller further receives a target anesthetic gas concentration and controls the flow valve to regulate the concentration of the anesthetic agent in the carrier gas and anesthetic agent combination.

3. The anesthetic vaporizer of claim 2, wherein the first sensor and the second sensor are time-of-flight ultrasonic sensors, the first sensor signal is a time of flight across the carrier gas conduit of carrier gas, and the second sensor signal is a time of flight across the carrier gas conduit of combined carrier gas and anesthetic agent.

4. The anesthetic vaporizer of claim 3, wherein the controller computes a target time of flight of the second sensor signal from an identification of the anesthetic agent, received target anesthetic gas concentration, and the first sensor signal.

5. The anesthetic vaporizer of claim 1, wherein the anesthetic source is a pressurized source of anesthetic agent.

6. The anesthetic vaporizer of claim 1, further comprising:
   a diversion conduit connected to the carrier gas conduit and to the anesthetic source, the diversion conduit being configured to open fluid communication between the carrier gas conduit and the anesthetic source.

7. The anesthetic vaporizer of claim 6, further comprising:
   a pressure regulator disposed in the carrier gas conduit between the diversion conduit and the anesthetic gas inlet; and
   a cut-off valve disposed in the diversion conduit;
   wherein the pressure regulator and the cut-off valve are controlled to selectively control the flow of carrier gas into the anesthetic source.

8. The anesthetic vaporizer of claim 7, wherein the anesthetic source is a sump of liquid anesthetic agent, and the pressure regulator and the cut-off valve are controlled to divert a portion of the carrier gas into the anesthetic source.

9. The anesthetic vaporizer of claim 7, wherein the anesthetic source is a pressurized anesthetic source and the pressure regulator and cut-off valve are controlled to close the diversion conduit to carrier gas flow.

10. The anesthetic vaporizer of claim 1, further comprising a manifold comprising the carrier gas conduit and the anesthetic gas inlet.

11. A system for the delivery of an anesthetic agent, the system comprising:
   a breathing circuit configured to deliver a combined gas to a patient;
   a carrier gas source, comprising a carrier gas;
   a carrier gas conduit connected to the carrier gas source and connected to the breathing circuit, the carrier gas conduit conveying a flow of carrier gas to the breathing circuit;
   an anesthetic source, comprising an anesthetic agent;

an anesthetic gas inlet in fluid communication between the anesthetic source and the breathing circuit, the anesthetic gas inlet conveying a flow of the anesthetic agent from the anesthetic source to the breathing circuit wherein the combined gas comprises the carrier gas and the anesthetic agent;

a flow valve in fluid communication between the anesthetic source and the anesthetic gas inlet, the flow valve operable to control the flow of the anesthetic agent through the anesthetic gas inlet;

a first sensor located along the carrier gas conduit, the first sensor produces a first sensor signal indicative of a composition of the carrier gas;

a second sensor located in the breathing circuit, the second sensor produces a second sensor signal indicative of a composition of the combined gas; and a controller that receives the first sensor signal and the second sensor signal, and calculates an anesthetic agent concentration of the combined gas from the first and second sensor signals, and the controller is connected to the flow valve and operates the flow valve to control the anesthetic agent concentration of the combined gas.

12. The system of claim 11, wherein the controller receives an indication of a target anesthetic agent concentration of the combined gas, and automatedly operates the flow valve until the second sensor signal is indicative of the target anesthetic agent concentration of the combined gas.

13. The system of claim 12, further comprising:
a diversion conduit in fluid communication between the carrier gas conduit and the anesthetic source;
a pressure regulator disposed within the carrier gas conduit between the diversion conduit and the anesthetic gas inlet; and
a cut-off valve disposed within the diversion conduit;
wherein the pressure regulator and cut-off valve are controlled to selectively divert a portion of the carrier gas into the anesthetic source.

14. The system of claim 13, wherein the anesthetic source is interchangeable between a sump of liquid anesthetic agent and a pressurized anesthetic source.

15. The system of claim 14, wherein when the anesthetic source is the sump of liquid anesthetic agent, and the pressure regulator and cut-off valve are controlled to divert the portion of the carrier gas into the sump and when the anesthetic source is the pressurized anesthetic source, the pressure regulator and cut-off valve are controlled to close the diversion conduit to carrier gas flow.

16. An anesthetic vaporizer, comprising:
a carrier gas conduit configured to deliver carrier gas;
an anesthetic source comprising an anesthetic agent;
an anesthetic gas inlet connecting the anesthetic source to the carrier gas conduit and configured to deliver an anesthetic agent to the carrier gas conduit, wherein the anesthetic agent and the carrier gas mix to form a combined gas;
a flow valve disposed between the anesthetic source and the anesthetic gas inlet operable to control the flow of anesthetic gas into the carrier gas conduit through the anesthetic gas inlet;
a first ultrasonic sensor in communication with the carrier gas conduit upstream of the anesthetic gas inlet and the first ultrasonic sensor produces a first time-of-flight signal indicative of a composition of the carrier gas;
a second ultrasonic sensor in communication with the carrier gas conduit downstream of the anesthetic gas inlet and the second ultrasonic sensor product a second time-of-flight signal indicative of a composition of the combined gas; and
a controller that receives the first time-of-flight signal and the second time-of-flight signal and operates the flow valve to control the composition of the combined gas.

17. The apparatus of claim 16, wherein the controller calculates a difference between the first time-of-flight signal and the second time-of-flight signal and calculates a combined gas composition.

18. The apparatus of claim 17, wherein the calculated difference is attributable to the flow of anesthetic.

19. The apparatus of claim 17, wherein the controller calculates the combined gas composition independent of one or more gases in the carrier gas.

20. The apparatus of claim 19, wherein the controller calculates an error signal between the calculated combined gas composition and a target combined gas composition and the controller operates the flow valve to minimize the error signal.

* * * * *